United States Patent
Nibhanipudi

(10) Patent No.: US 11,969,400 B2
(45) Date of Patent: Apr. 30, 2024

(54) IBUPROFEN FOR SYMPTOMATIC TREATMENT OF DIARRHEAS IN HIV PATIENTS

(71) Applicant: Kumara V. Nibhanipudi, Scarsdale, NY (US)

(72) Inventor: Kumara V. Nibhanipudi, Scarsdale, NY (US)

( * ) Notice: Subject to any disclaimer, the term of this patent is extended or adjusted under 35 U.S.C. 154(b) by 0 days.

(21) Appl. No.: 17/209,324

(22) Filed: Mar. 23, 2021

(65) Prior Publication Data

US 2022/0304961 A1    Sep. 29, 2022

(51) Int. Cl.
*A61K 31/4422*    (2006.01)
*A61K 31/192*    (2006.01)
*A61P 1/12*    (2006.01)

(52) U.S. Cl.
CPC .............. *A61K 31/192* (2013.01); *A61P 1/12* (2018.01)

(58) Field of Classification Search
CPC .................................................. A61K 31/192
See application file for complete search history.

(56) References Cited

U.S. PATENT DOCUMENTS

| | | | |
|---|---|---|---|
| 2003/0178031 A1* | 9/2003 | Du Pen | A61B 5/00 128/898 |
| 2011/0124730 A1* | 5/2011 | Atkinson | A61P 25/04 514/570 |
| 2013/0109754 A1* | 5/2013 | Senosiain | A61K 31/198 514/565 |
| 2014/0112978 A1* | 4/2014 | Su | A61K 9/127 560/103 |
| 2019/0161529 A1* | 5/2019 | Greenberg | C07K 14/705 |

FOREIGN PATENT DOCUMENTS

WO    WO 02/086136    * 10/2002

OTHER PUBLICATIONS

Rampal et. al. (The Journal of International Medical Research (2002) 30:301-308). (Year: 2002).*
Martino et. al. (Drugs (2017) 77:1295-1311). (Year: 2017).*
Drugs.com (Nov. 12, 2020) (Year: 2020).*
Thiagarajah et. al. (Clinical Pharmacology and Therapeutics (2012) 92:287-290),. (Year: 2012).*
Frampton (Drugs (2013) 73:1121-1129). (Year: 2013).*
Devor et. al. (J. Clin. Invest. (1998) 102:679-687). (Year: 1998).*
Moon et. al. (Pharmacol. Res. (2015) 102:107-112). (Year: 2015).*
Dikman, et al., "Human Immunodeficiency Virus-Associated Diarrhea: Still an Issue in the Era of Antiretroviral Therapy," Dig. Dis. Sci (2015) 60:2236-2245.

* cited by examiner

*Primary Examiner* — Marcos L Sznaidman
(74) *Attorney, Agent, or Firm* — MaxGoLaw PLLC

(57) ABSTRACT

A method of treating noninfectious diarrhea in an HIV positive subject includes administering a dose of ibuprofen to the HIV positive subject at regular intervals until stool consistency is improved, diarrhea is alleviated, or the number of bowel movements per day are decreased. The dose is 400 mg of ibuprofen administered every 6 hours. The method may additionally include diagnosing the subject with noninfectious diarrhea, determining the subject does not have certain comorbidities, and/or determining that the subject is not taking any non-steroidal anti-inflammatory drugs. The method may additionally include after administering the ibuprofen, administering a clear liquids diet to the subject, administering an electrolyte supplement to the subject, and/or monitoring the subject for any bleeding from the gastrointestinal tract until stool consistency is improved, until diarrhea is alleviated, or until the number of bowel movements per day are decreased.

7 Claims, 1 Drawing Sheet

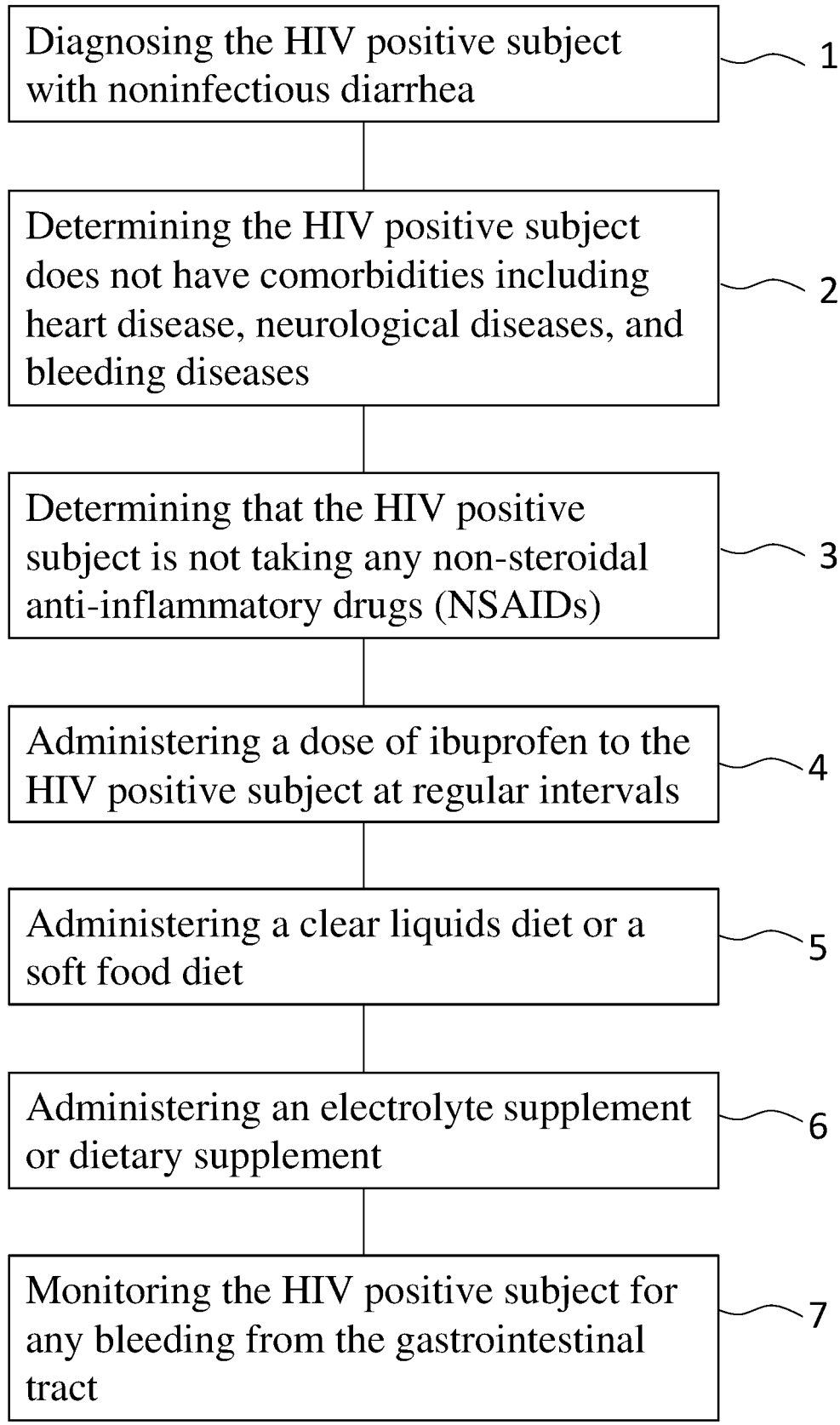

IBUPROFEN FOR SYMPTOMATIC TREATMENT OF DIARRHEAS IN HIV PATIENTS

FIELD OF THE INVENTION

The present invention relates to treatment of diarrhea in patients with human immunodeficiency virus (HIV). More particularly, it relates to treatment of noninfectious, chronic diarrhea in patients with HIV using ibuprofen followed by a liquid diet.

BACKGROUND OF THE INVENTION

Advances in the treatment of human immunodeficiency virus (HIV) and acquired immunodeficiency syndrome (AIDS), such as antiretroviral therapy (ART), have transformed this disease into a chronic illness. As a result, individuals with HIV have a longer life expectancy. When HIV is treated early and aggressively, life expectancy approaches that of uninfected individuals. However, over half of patients with HIV experience diarrhea that contributes negatively to quality of life and adherence to ART. Opportunistic infectious agents that cause diarrhea in patients with HIV span the array of protozoa, fungi, viruses, and bacteria. With global use of ART, the incidence of diarrhea because of opportunistic infections has decreased; however, the incidence of noninfectious diarrhea has increased. The etiology of noninfectious diarrhea in patients with HIV is multifactorial and includes ART-associated diarrhea and gastrointestinal damage related to HIV infection (i.e., HIV enteropathy). A basic algorithm for the diagnosis of diarrhea in patients with HIV includes physical examination, a review of medical history, assessment of HIV viral load and CD4+ T cell count, stool microbiologic assessment, and endoscopic evaluation, if needed. For patients with negative diagnostic results, the diagnosis of noninfectious diarrhea may be considered. Noninfectious diarrhea is defined as pathogen-negative diarrhea and includes ART-associated diarrhea, GI damage related to HIV infection (i.e., HIV enteropathy), and many causes mirroring those seen in gender- and age-matched patients without HIV infection.

Typical therapies for any patient with diarrhea include hydration via intravenous and/or oral routes, repletion of electrolytes, and treating the underlying cause, if possible. Additional therapies for treatment of common acute diarrhea are widely known. For example, use of aspirin and other non-steroidal anti-inflammatory drugs (NSAIDS) such as indomethacin and ibuprofen are known to reduce acute febrile diarrhea in children.

However, managing chronic noninfectious diarrhea in patients with HIV is far more complicated. Currently, noninfectious diarrhea in patients with HIV can be managed by modifying ART and controlling symptoms with lifestyle modification. However, clinical guidelines for patients with HIV recommend careful evaluation of the symptoms and symptomatic management of ART-related adverse events (AEs) (e.g., diarrhea) before switching or modifying ART, with supportive care (e.g., antidiarrheals) generally allowing for continuation of prescribed ART therapy. However, cessation of ART ("drug holiday") is generally not advised as a management strategy. Pharmacologic options for the treatment of noninfectious diarrhea are primarily supportive; however, the use of many unapproved agents is based on unstudied and anecdotal information. In addition, these agents can be associated with treatment-limiting AEs, such as drug-drug interactions with ART regimens, abuse liability, and additional gastrointestinal AEs.

Existing antidiarrheal medications used for treatment of noninfectious diarrhea can be divided into several classes: adsorbents, antimotility agents, and antisecretory agents. Adsorbent drugs bind bacterial toxins, fluids, and other compounds in the intestines to improve stool consistency. Drugs in this category include bismuth subsalicylate, kaolin/pectin, and attapulgite (aluminum magnesium silicate purified from clay). Data on the use of adsorbents in patients with HIV are limited and show the efficacy is not better than placebo in the management of diarrhea.

Antimotility agents include loperamide, diphenoxylate/atropine, and tincture of opium. These agents act upon opioid receptors in the gut to slow motility by decreasing peristalsis and increasing tone in the large intestine. This allows for greater fecal transit time and therefore longer time for water absorption. However, some antimotility agents cross the blood-brain barrier and can cause central effects analogous to other opioid agonists, carry a potential for abuse, and may interact with ART agents. Accordingly, such agents are not suitable for long-term therapy.

Antisecretory agents, such as octreotide, racecadotril, and crofelemer, directly inhibit secretory processes within enterocytes. However, published data conflict about the efficacy of such antisecretory agents in treating diarrhea in patients with AIDS. Oral racecadotril is an enkephalinase inhibitor, which decreases the breakdown of endogenous gut opioids, thereby decreasing the secretion of water and electrolytes into the gut lumen. However, racecadotril is not currently available in the USA.

Orally administered crofelemer is a dual inhibitor of cAMP-stimulated cystic fibrosis transmembrane conductance regulator (CFTR) and calcium-stimulated calciumactivated chloride channels (CaCC) in the gut. Crofelemer is a minimally absorbed GI drug derived from the latex of the Croton lechleri tree. Currently, crofelemer is the only agent approved in the USA for the symptomatic relief of noninfectious diarrhea in patients with HIV on ART. While crofelemer seems to be well tolerated in treated patients with the only adverse effects found in clinical studies being mild gastrointestinal effects at the same level as under placebo, this treatment agent is exceedingly expensive. That is, in April 2020 the pharmaceutical company that produces crofelemer raised the price of that drug by more than three times from $669 for 60 pills to $2,206 for the same number of pills.

Thus, there exists a need for an effective, available, and cost-effective treatment of noninfectious, chronic diarrhea in patients with HIV that reduces the number of loose stools and decreases the occurrence of dehydration, while avoiding treatment-limiting adverse events, such as drug-drug interactions with ART regimens, abuse liability, and additional gastrointestinal adverse events.

SUMMARY OF THE INVENTION

The present invention provides a method of treating noninfectious diarrhea in an HIV positive subject that includes administering a dose of ibuprofen to the HIV positive subject at regular intervals until stool consistency is improved, until diarrhea is alleviated, or until the number of bowel movements per day are decreased. According to embodiments, the dose is 400 mg of ibuprofen administered every 6 hours. According to embodiments, the inventive method additionally includes initially diagnosing the HIV positive subject with noninfectious diarrhea prior to administering the ibuprofen, determining the HIV positive subject does not have comorbidities including heart disease, neurological diseases, and bleeding diseases prior to administering the ibuprofen and/or determining that the HIV positive subject is not taking any non-steroidal anti-inflammatory drugs (NSAIDs) prior to administering the ibuprofen. According to embodiments, the inventive method additionally includes after administering the ibuprofen, administering a clear liquids diet or a soft food diet to the HIV positive subject, administering an electrolyte supplement or dietary supplement to the HIV positive subject, and/or monitoring the HIV positive subject for any bleeding from the gastrointestinal tract until stool consistency is improved, until diarrhea is alleviated, or until the number of bowel movements per day are decreased.

BRIEF DESCRIPTION OF THE DRAWINGS

The present invention is further detailed with respect to the following drawings that are intended to show certain aspects of the present invention but should not be construed as a limit on the practice of the present invention.

FIG. 1 shows a flowchart showing the steps of a method of treating noninfectious, chronic diarrhea in patients with HIV according to embodiments.

DESCRIPTION OF THE INVENTION

The present invention has utility as an effective, available, and cost-effective treatment of noninfectious, chronic diarrhea in patients with HIV that reduces the number of loose stools and decreases the occurrence of dehydration, while avoiding treatment-limiting adverse events, such as drug-drug interactions with ART regimens, abuse liability, and additional gastrointestinal adverse events.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

According to embodiments the present invention provides a method of treating noninfectious, chronic diarrhea in a patient with HIV. According to embodiments, the method of treating noninfectious diarrhea includes improving stool consistency in an HIV positive subject, alleviating watery diarrhea in an HIV positive subject, or decreasing the number of bowel movements per day in an HIV positive subject. The inventive method includes administering a dose of ibuprofen to the HIV positive subject at regular intervals until the subject's diarrhea condition is improved, as shown in step 4 of FIG. 1. It has been found that ibuprofen surprisingly treats noninfectious diarrhea in HIV positive patients based on the fact that ibuprofen inhibits prostaglandins. According to embodiments, the HIV positive subject's diarrhea condition is considered to be improved when the subject's stool consistency is improved, the subject's watery diarrhea is alleviated, or the subject's number of bowel movements per day are decreased.

According to embodiments, the administered dose is between 100 and 500 mg of ibuprofen, and more particularly, is 400 mg of ibuprofen. According to embodiments, the dose is administered at regular intervals of between 2 and 8 hours, and more particularly the regular intervals of administration are 6 hour intervals. That is, according to embodiments, the inventive method includes administering 400 mg of ibuprofen to the HIV positive subject every 6 hours until the subject's diarrhea condition is improved.

According to embodiments, the inventive method of treating noninfectious diarrhea in an HIV positive subject additionally includes initially diagnosing the HIV positive subject with noninfectious diarrhea prior to administering the ibuprofen, as shown at step 1 in FIG. 1. As used herein, noninfectious diarrhea is defined as pathogen-negative diarrhea and includes ART-associated diarrhea and GI damage related to HIV infection (i.e., HIV enteropathy). To diagnose the HIV positive subject with noninfectious diarrhea, a care provider may conduct a physical examination, a review of medical history, assessment of HIV viral load and CD4+ T cell count, stool microbiologic assessment, and/or endoscopic evaluation.

According to embodiments, the inventive method of treating noninfectious diarrhea in an HIV positive subject additionally includes determining the HIV positive subject does not have comorbidities including heart disease, neurological diseases, and bleeding diseases prior to administering the ibuprofen, as shown in step 2 of FIG. 1. To determined that the HIV positive subject does not have comorbidities including heart disease, neurological diseases, and bleeding diseases, a care provider may review the subject's medical history and/or may conduct a physical examination of the subject. Furthermore, determining that the HIV positive subject does not have certain comorbidities may additionally include determining what comorbidities the subject does have.

According to embodiments, the inventive method of treating noninfectious diarrhea in an HIV positive subject additionally includes determining that the HIV positive subject is not taking any non-steroidal anti-inflammatory drugs (NSAIDS) prior to administering the ibuprofen, as shown in step 3 of FIG. 1. Generally, NSAIDS include but are not limited to aspirin, celecoxib (Celebrex), diclofenac (Cambia, Cataflam, Voltaren-XR, Zipsor, Zorvolex), diflunisal (Dolobid—discontinued brand), etodolac (Lodine—discontinued brand), ibuprofen (Motrin, Advil), indomethacin (Indocin), ketoprofen (Active-Ketoprofen [Orudis—discontinued brand]), ketorolac (Toradol—discontinued brand), nabumetone (Relafen—discontinued brand), naproxen (Aleve, Anaprox, Naprelan, Naprosyn), oxaprozin (Daypro), piroxicam (Feldene), salsalate (Disalsate [Amigesic—discontinued brand]), sulindac (Clinoril—discontinued brand), tolmetin (Tolectin—discontinued brand). To determined that the HIV positive subject is not taking any NSAIDS, a care provider may review the subject's medical history, discuss any prescription and non-prescription medications the subject has consumed recently, and/or conduct urine or blood analysis.

According to embodiments, the inventive method of treating noninfectious diarrhea in an HIV positive subject additionally includes administering a clear liquids diet or a soft food diet to the HIV positive subject after administering the ibuprofen, as shown in step 5 of FIG. 1. A clear liquid diet helps maintain adequate hydration, provides some important electrolytes, such as sodium and potassium, and gives some energy while the subject's gastrointestinal tract is given some time to recover. According to embodiments, a clear liquids diet includes water (plain, carbonated or flavored); fruit juices without pulp, such as apple or white grape juice; fruit-flavored beverages, such as fruit punch or lemonade; carbonated drinks, including dark sodas (cola and root beer); gelatin; tea or coffee without milk or cream; strained tomato or vegetable juice; sports drinks; clear, fat-free broth (bouillon or consomme); honey or sugar; hard candy, such as lemon drops or peppermint rounds; and ice pops without milk, bits of fruit, seeds or nuts. Essentially, acceptable food and beverages are those that are easily digested and leave no undigested residue in the intestinal tract. Clear liquids and foods may be colored so long as one is able to see through the substance. Foods are considered liquid if they partly or completely melt to liquid at room temperature. However, solid food is not acceptable as part of the clear liquid diet.

According to embodiments, the inventive method of treating noninfectious diarrhea in an HIV positive subject additionally includes administering an electrolyte supplement or dietary supplement to the HIV positive subject after administering the ibuprofen, as shown in step 6 of FIG. 1. The electrolyte supplement or dietary supplement helps maintain adequate hydration, provides some important electrolytes, such as sodium and potassium, and gives provides some additional nutrition while the subject's gastrointestinal tract is given some time to recover and/or while the subject is one a clear liquids diet that is unable to provide the subject with adequate calories and nutrients. According to embodiments, the electrolyte supplement is Pedialyte.

According to embodiments, the inventive method of treating noninfectious diarrhea in an HIV positive subject additionally includes monitoring the HIV positive subject for any bleeding from the gastrointestinal tract after administering the ibuprofen, as shown in step 7 of FIG. 1. According to embodiments, monitoring for any bleeding from the gastrointestinal tract includes inspecting the subject's stool and/or monitoring the subject's blood for indications of bleeding such as a decrease in hemoglobin.

The invention is further illustrated by way of Example.

HIV positive subjects who present with noninfectious diarrhea are enrolled in a study. All enrollees are randomly divided into two groups A (Acetaminophen) and B (Ibuprofen) and treated for 24 hours. They receive a double-blinded suspension of either Acetaminophen or Ibuprofen during the study period. The enrollees are instructed to consume only a clear liquid diet during the study period. After 24 hours, the number of loose stools since last visit and status of hydration are reassessed. In addition, enrollees are examined and assessed for any possible side effects of the medications.

A total of 84 patients are enrolled into the study. Both drug categories has 42 (50%) enrollees. Two patients are lost to follow up in each group. The average number of stools on the first visit (day 1) in group A (Acetaminophen) is 5.12 and the average number of stools in group B (ibuprofen) is 5.25. Twenty-four hours later, the average number of stools, in group A is 3.45 (1-5) and the average number of stool in group B, is 1.9 (0-4). The two-tailed p-value was <0.0001 with a confidence interval at 95% (1.44-2.6).

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention but is not meant to be a limitation upon the practice thereof. The following claims, including all equivalents thereof, are intended to define the scope of the invention.

The invention claimed is:

1. A method of alleviating watery diarrhea in an HIV positive subject having noninfectious diarrhea caused by antiretroviral therapy, HIV enteropathy, or a combination thereof, comprising:
   administering a dose of ibuprofen to the HIV positive subject having noninfectious diarrhea and taking antiretroviral therapy, said dose taken at regular intervals of at least once per day until watery diarrhea is alleviated with the proviso that the HIV positive subject is not taking any non-steroidal anti-inflammatory drugs (NSAIDS) prior to administering the ibuprofen.

2. The method of claim 1 wherein the dose is 400 mg of ibuprofen.

3. The method of claim 1 wherein the regular intervals are 6 hour intervals.

4. The method of claim 1 further comprising determining the HIV positive subject does not have comorbidities including heart disease, neurological diseases, and bleeding diseases prior to administering the ibuprofen.

5. The method of claim 1 further comprising after administering the ibuprofen, administering a clear liquids diet or a soft food diet to the HIV positive subject until watery diarrhea is alleviated.

6. The method of claim 1 further comprising after administering the ibuprofen, administering an electrolyte supplement or dietary supplement to the HIV positive subject until watery diarrhea is alleviated.

7. The method of claim 1 further comprising after administering the ibuprofen, monitoring the HIV positive subject for any bleeding from the gastrointestinal tract until watery diarrhea is alleviated.

* * * * *